United States Patent [19]
Papaioannou

[11] Patent Number: 5,941,827
[45] Date of Patent: Aug. 24, 1999

[54] LOCALIZATION OF AN OBJECT IN A TURBID MEDIUM USING RADIATION OF DIFFERENT WAVELENGTHS

[75] Inventor: Dimitrius Papaioannou, Athene, Greece

[73] Assignee: U.S. Philips Corporation, New York, N.Y.

[21] Appl. No.: 08/973,135

[22] PCT Filed: Apr. 1, 1997

[86] PCT No.: PCT/IB97/00324

§ 371 Date: Dec. 1, 1997

§ 102(e) Date: Dec. 1, 1997

[87] PCT Pub. No.: WO97/36539

PCT Pub. Date: Oct. 9, 1997

[30] Foreign Application Priority Data

Apr. 2, 1996 [EP] European Pat. Off. .............. 96200895

[51] Int. Cl.[6] ...................................................... A61B 5/00
[52] U.S. Cl. .......................... 600/473; 600/476; 356/432; 250/330
[58] Field of Search .................................... 600/473, 476, 600/310, 475, 477; 356/432, 433, 434, 435, 345, 349; 250/330, 332, 339.01

[56] References Cited

U.S. PATENT DOCUMENTS

| | | |
|---|---|---|
| 5,088,493 | 2/1992 | Giannini et al. . |
| 5,090,415 | 2/1992 | Yamashita et al. . |
| 5,203,339 | 4/1993 | Knuttel et al. . |
| 5,371,368 | 12/1994 | Alfano et al. . |
| 5,416,582 | 5/1995 | Knutson et al. . |
| 5,664,574 | 9/1997 | Chance . |
| 5,673,701 | 10/1997 | Chance . |
| 5,722,406 | 3/1998 | Papaioannou . |
| 5,722,407 | 3/1998 | Klingenbeck-Regn et al. . |
| 5,746,210 | 5/1998 | Benaron et al. . |
| 5,772,588 | 6/1998 | Miwa et al. . |
| 5,782,755 | 7/1998 | Chance et al. . |

Primary Examiner—William E. Kamm
Assistant Examiner—Shawna J. Shaw
Attorney, Agent, or Firm—Dwight H. Renfrew, Jr.

[57] ABSTRACT

A system for detecting an object (1) in a turbid medium (2) comprises a radiation source (3) for irradiating the turbid medium with radiation components of different wavelengths, preferably in the range between 600 nm and 1 μm. The radiation components are amplitude modulated, preferably in anti-phase. The radiation form the turbid medium is received by a photodetector (4) which is sensitive for the different wavelengths. Inhomogeneities in the turbid medium influence the superposition of the amplitude modulations at the photodetector, so that the photodetector outputs a signal that contains information on the presence and/or location of an object in the turbid medium.

21 Claims, 2 Drawing Sheets

LOCALIZATION OF AN OBJECT IN A TURBID MEDIUM USING RADIATION OF DIFFERENT WAVELENGTHS

BACKGROUND OF THE INVENTION

1. Field of the Invention

The invention relates to a system for localizing an object in a turbid medium. The invention also relates to a method for localizing an object in a turbid medium.

Such a system is advantageously used for imaging human or animal tissue. In particular, in the field of mammography detection of an object in a turbid medium is employed to detect a tumour in a woman's breast.

2. Description of the Related Art

Such a system is known from the article *Highly sensitive object location in tissue models with linear in-phase and anti-phase multi-element optical arrays in one and two dimensions,* by B. Chance et al. in the Proceedings of the National Academy of Science USA Vol. 90 (1993) 3423–3427.

The known system comprises spatially separated light sources emitting substantially the same wavelength. The light sources are amplitude modulated with essentially the same frequency and with a phase difference of about 180°. When the known system would illuminate a homogeneous medium the amplitude modulations cancel along the perpendicular bisector of the separation of the two sources. Any inhomogeneity like an object in the turbid medium causes a deviation from the cancellation of the Amplitude modulation along the perpendicular bisector and as a consequence a signal is detected by a photodetector set-up on the perpendicular bisector. However, the known system does not provide information pertaining to the composition of the object. Hence, the known system is e.g. unable to distinguish a malignant cancerous tumour from a benign tumour.

SUMMARY OF THE INVENTION

An object of the invention is to provide a system for detecting an object in a turbid medium which is substantially sensitive for the composition of the object.

This object is achieved by a system for detecting an object in a turbid medium according to the invention comprising a radiation source for irradiating the turbid medium with radiation components having a first and a second wavelength, respectively, the radiation components of the first and second wavelength being amplitude modulated at substantially equal modulation frequencies, the amplitude modulation of the radiation components of the first and second wavelength having a predetermined phase difference, and a photodetector arranged to detect radiation from the turbid medium.

The radiation source irradiates the turbid medium and radiation having passed through at least a part of the turbid medium is detected by the photodetector. When the turbid medium would be homogeneous the amplitude modulations would superpose at the photodetector in a predetermined way. That superposition is represented by a predetermined photodetector signal. In particular, the superposition of the amplitude modulations would be predetermined by the absorption of the radiation components of the first and second wavelength by the turbid medium and the distance between the position of incidence of the radiation components and the photodetector. The object causes a deviation from the predetermined superposition and the ensuing deviation of the actual photodetector signal from the predetermined photodetector signal contains information on the object. In particular the deviation of the superposition is caused by a difference of the dependence of the absorption on the wavelengths for the turbid medium and for the object. For example, a cancerous tumour in a woman's breast has a different absorption behaviour as a function of the wavelengths as compared to the healthy breast tissue.

The deviation of the actual photodetector signal from the predetermined photodetector signal represents both the position and at least some aspects of the composition of the object. The deviation comprises spectroscopic information pertaining to the object, which represents at least some aspects of its composition. The deviation of the superposition of the amplitude modulations is caused substantially throughout the region in the turbid medium that is traversed by the radiation components. Hence, the system according to the invention is able to detect very small objects and/or objects that do not differ much from the surrounding turbid medium, e.g. very small tumors that differ only slightly from the surrounding healthy tissue.

In order that a significant difference occurs between the predetermined photodetector signal pertaining to a homogeneous turbid medium and the actual photodetector signal pertaining to the object in the turbid medium the photodetector is substantially sensitive for both the first and second wavelength. Preferably, the radiation components each have a wavelength in the range from 600 nm to 1 $\mu$m, which means that infrared radiation or visible light is used. The radiation having a wavelength in this range is non-ionizing and as far as presently known causes hardly any or no damage to healthy tissue. Moreover, in this range the scattering of radiation is scattered sufficiently weakly to achieve adequate spatial resolution in order to enable detection and localization of an object, absorption being sufficiently low so as to allow a substantial intensity of the radiation components to reach the photodetector in order that the photodetector signal has an adequate signal-to-noise ratio.

In a further preferred embodiment of a system according to the invention the predetermined phase difference is substantially equal to 180°.

The radiation components of the first and second wavelengths are amplitude modulated in anti-phase. Both radiation components are incident on the turbid medium at the same position. In a homogeneous turbid medium of which the absorptivities and scattering at the first and second wavelengths are substantially the same the amplitude modulations of the respective radiation components would cancel one another everywhere in the turbid medium. Thus, if no object were present in the turbid medium, the predetermined photodetector signal would comprise practically only a DC component. When there is an inhomogeneity, such as the object, in the turbid medium, then the amplitude modulations do not fully cancel and the actual photodetector signal comprises an AC component having the frequency of the amplitude modulation. It is quite simple to measure the AC component. Moreover, as the predetermined photodetector signal for a homogeneous turbid medium is a DC signal, it is not required to actually form the predetermined photodetector signal.

In a further preferred embodiment of a system according to the invention the photodetector has a sensitivity wavelength range encompassing the first and second wavelength.

Although a photodetector may be used which comprises separate detector portions for detecting the radiation components of the first and the second wavelength, preferably a photodetector is employed having a photosensitive element that has a sensitivity bandwidth that is wide enough to contain both the first and second wavelength. With such a wide-band photodetector it is easy to detect both radiation components from the same position in the turbid medium. Hence, it is avoided that the photodetector detects radiation components leaving the turbid medium from different positions, giving rise to a false AC signal not related to the object. Moreover, the wide-band photodetector is suitable for use when the radiation components contain wavelengths in bands around the first and the second wavelength, respectively. This is because hardly any radiation from the turbid medium is lost when the wide-band photodetector is employed, thus enhancing the sensitivity of the system for small objects that do not differ much from the turbid medium.

In a further preferred embodiment of a system according to the invention the amplitude modulation is substantially a square wave modulation.

This corresponds to consecutively supplying one of the radiation components of while blocking the other radiation component. This is most easily achieved by providing separate sources for generating the respective radiation components. In that case a square wave modulation having a phase difference of 180° is achieved by turning on one source while turning off the other.

A further object of the invention is to provide a system for detecting and localizing an object in a turbid medium, which system is also sensitive to the composition of the object.

In a further preferred embodiment of a system according to the invention the photodetector has a radiation receiving portion and the system comprises a compression mechanism for compressing the turbid medium, a displacement device for moving a radiation emitting surface with respect to the turbid medium and a radiation receiving portion of the photodetector being arranged opposite the radiation emitting face.

The radiation generated by the radiation source leaves the source from its radiation emitting surface so as to irradiate the turbid medium. The radiation having passed at least partly through the turbid medium is picked-up by the receiving portion of the photodetector. The compression apparatus arranges the turbid medium substantially in a slab geometry. The turbid medium, i.e. the woman's breast, is scanned by moving the radiation emitting face of the radiation source with respect to the turbid medium. In that way the turbid medium is irradiated from successive positions on at least part of the surface of the turbid medium. During scanning of the turbid medium either a single receiving portion is moved together with the radiation emitting surface such that the separation between the radiation receiving portion and the radiation emitting surface remains substantially constant, or a plurality of radiation receiving faces may be employed such that during scanning successive receiving portions are activated, such that the separation between the radiation emitting sur face and an active receiving portion is substantially constant. Thus, it is achieved that during scanning the length of the path that the radiation traverses through the turbid medium is accurately kept constant. Hence, differences between the amplitudes of the first and second radiation components at the photodetector which are caused by a dependence on the wavelength of the absorptivity of the turbid medium itself are significantly avoided. Successive photodetector signals contain information on the position and composition of the object. Preferably, the amplitude modulation depths of the respective radiation components are adjusted in correspondence with the absorptivities for the radiation components of the first and second wavelengths in the turbid medium. In order to achieve that for a homogeneous turbid medium the predetermined photodetector signal substantially only contains a DC component, the amplitude modulation depths of the respective radiation components are adjusted in correspondence with the sensitivity of the photodetector for the first and second wavelength and That is, should the photodetector be less sensitive for the first wavelength than for the second wavelength, then the modulation depth of the radiation component of the first wavelength is made larger than the modulation depth of the radiation component of the second wavelength.

A further preferred embodiment of a system according to the invention comprises a source fiber arranged to guide radiation from the radiation source to the turbid medium and a plurality of detector fibers arranged to guide radiation from respective positions of the turbid medium, to the photodetector.

The source fiber sends both radiation components into the turbid medium. Each of the detector fibers collects radiation from separate positions around the turbid medium. Hence, the photodetector receives radiation having traversed separate paths through the turbid medium. Thus, the actual photodetector signal contains spatial and spectroscopic information on the object in the turbid medium. The actual photodetector signal is suitably processed so as to form an image signal which represents the location and/or structure of the object. The signals from separate detector fibers may be processed in parallel in order to generate the image signal. The image signal may be employed to reproduce the object and/or its position and composition in the turbid medium in an image e.g. on a monitor or on a hard copy.

It is noted that instead of employing a single source fiber and a multitude of detector fibers it is also possible to employ a multitude of source fibers and a single detector fiber.

In a further preferred embodiment of a system according to the invention the photodetector is a charge-coupled device (CCD).

The detector fibers are coupled to separate photosensitive elements of the photodiode array or CCD-sensor so that reeve photosensitive elements receive radiation from various positions of the turbid medium. The photosensitive elements convert incident radiation, such as (infrared) light into electrical charges. When a CCD-sensor is employed, these electrical charges are easily read-out by transfering them in a bucket-brigade fashion to a read-out register. From the read-out charges the actual photodetector signal is derived. The signal-to-noise ratio of the photodetector signal may be improved by cooling the array of photosensors or the CCD-sensor, so as to reduce electric charges released by thermal excitations.

In a further preferred embodiment of a system according to the invention the photodetector comprises a read-out circuit that is arranged to operate synchronously with the amplitude modulation.

The photodetector supplies successive photodetector signals corresponding to the respective radiation components having the first and second wavelengths. The difference between these successive signals includes spectral information pertaining the object.

In a further preferred embodiment of a system according to the invention the read-out circuit comprises a subtraction unit.

The read-out circuit outputs electrical charges corresponding to the respective radiation components from the turbid medium. From these electrical charges, there are derived respective photodetector signals corresponding to the respective radiation components. The subtraction unit is arranged to form the image signal of which the signal level equals the difference between the signal levels of the successive photodetector signals. The image signal represents the position of the object in the turbid medium.

Another object of the invention is to provide a method for detecting an object in a turbid medium which is substantially sensitive for the composition of the object.

According to the invention, a method for detecting an object in a turbid medium comprises that the medium is irradiated with radiation components having a first and a second wavelength, respectively, the radiation components of the first and second wavelength being amplitude modulated at substantially equal modulation frequencies, the amplitude modulation of the radiation components of the first and second wavelength having a predetermined phase difference, and radiation from the turbid medium is detected.

The method provides for detection and for deriving at least part of the composition of the object in the turbid medium with good sensitivity. Namely, the method according to the invention provides spectroscopic information on the object which is detected and/or localized. Even small objects that do not differ much form the surrounding turbid medium are accurately localized.

Notably, the method according to the invention may also advantageously be employed to detect the distribution of suitable pharmacological tracer materials or compositions. Suitably chosen tracers concentrate predominantly in malignant tracers and such a tracers may be chosen such that at one of the first or second wavelengths, its absorptivity differs considerably from the absorptivity of the surrounding healthy tissue These and other aspects of the invention will be illustrated by way of example with reference to the embodiment described hereinafter and with reference to the accompanying drawing.

DESCRIPTION OF THE PREFERRED EMBODIMENTS

Figure 1:
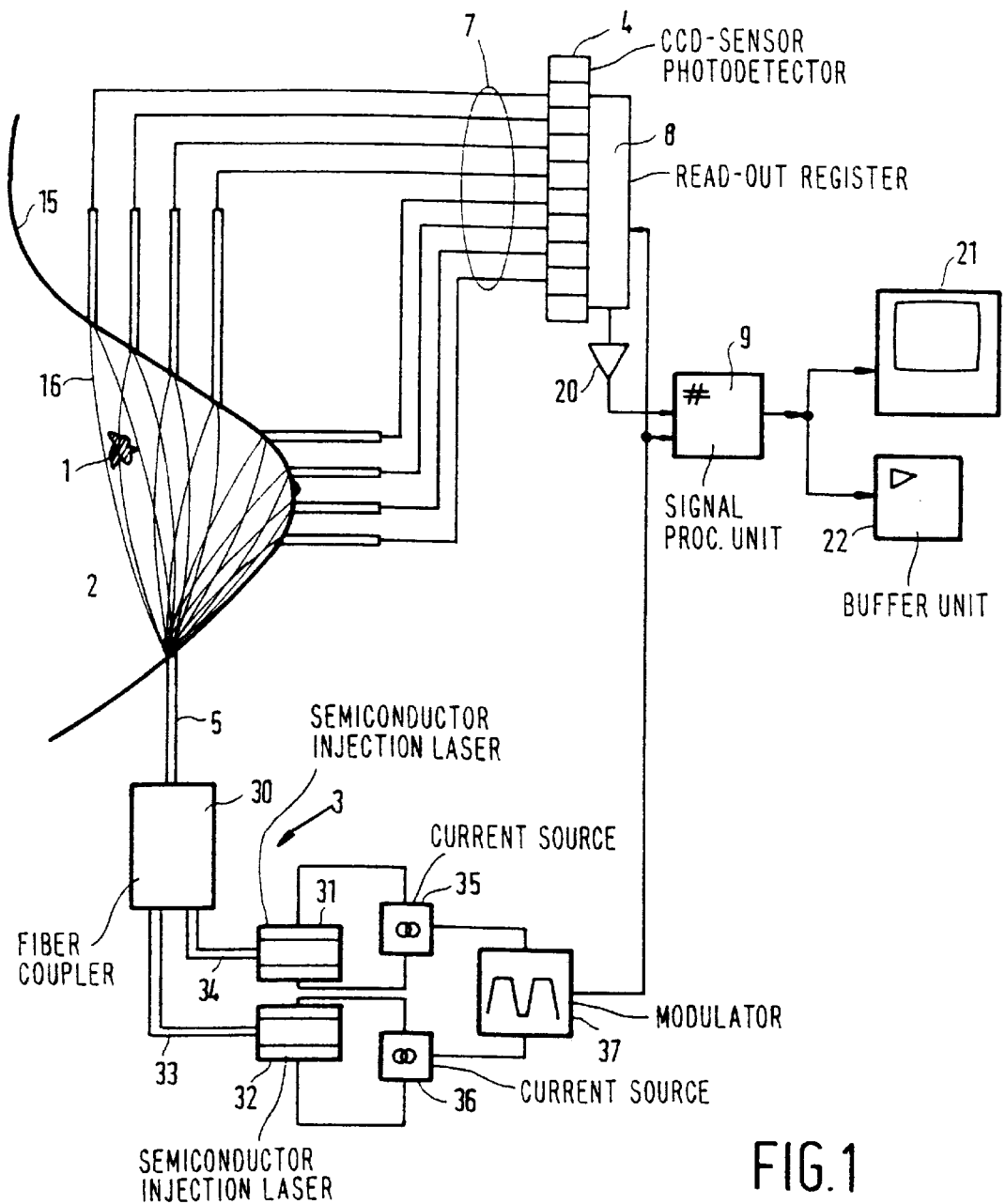
FIG. 1 shows schematically of a mammography apparatus comprising a first embodiment of a system for detecting an object in a turbid medium according to the invention.

FIG. 1 shows schematically a mammography apparatus comprising a system for detecting an object in a turbid medium according to the invention. The purpose of such a mammography apparatus is to detect inhomogeneities in the tissue of a woman's breast. For example such inhomogeneities may be micro-vascularizations, i.e. high concentrations of small bloodvessels, which are formed around a malignant tumor, or such a tumour itself. In particular the system according to the invention aims at detecting and localizing such lesions when they are quite small so that any carcinomae may be discovered in an early stage of the pathology, but without exposing the woman to be examined to the risk of ionizing radiation such as x-rays.

The source fiber 5 and detector fibers 7 are arranged along the circumference 15 of the woman's breast. Radiation of two different wavelengths is radiated into the breast tissue which is in fact the turbid medium 2. Because of scattering each of the detector fibers 7 receives light from a more or less banana-shaped region 16. Radiation having a wavelength in the range from 600 nm to 1 $\mu$ is suitable because in that range both absorption in the breast tissue is sufficiently low in order that a substantial intensity reaches the detector fibres and scattering of radiation in the breast tissue is sufficiently low so as to achieve an adequate spatial resolution for detecting the object. If infrared radiation having a wavelength substantially larger than 1 $\mu$m would be employed absorption by water would cause insufficient infrared radiation intensity at the photodetector. Light having a wavelength of less than 600 nm (orange) would be scattered so strongly in the breast tissue that spatial resolution becomes insufficient to detect the object. Particularly favorable results are achieved with radiation having a wavelength in the range between 780 nm and 940nm. Further, infrared radiation in the range between 600 nm and 1 $\mu$m is conveniently obtained by using semiconductor injection lasers.

The radiation received by the separate detector fibers 7 is supplied to a photodetector which is in fact a CCD-sensor 4. The radiation from the detector fibers 7 is converted into electrical charges in the photosensitive elements of the CCD-sensor. The electrical charges are read-out by way of a read-out circuit 8, which is in fact a read-out register 8, to an amplifier 20. The amplifier 20 derives the photodetector signal from the read charges and supplies the photodetector signal to a signal processing unit 9. The photodetector signal contains information on the location and the composition of the object 1. The photodetector signal is converted to an image signal by the signal processing unit. Notably, the image signal is formed as an electronic video signal. The electronic video signal may be supplied to a monitor 21 on which the information concerning the object 1 in the turbid medium of the breast tissue is made visible. The electronic video signal may also be supplied to a buffer unit 22 to be stored before further processing.

The radiation source 3 comprises a fiber coupler 30 to which two separate semiconductor injection lasers 31 and 32 are coupled. The output light from these lasers 31, 32 is supplied to the fiber coupler by way of optical fibers 33, 34. The separate semiconductor injection lasers emit infrared light of different wavelengths in the range between 780 nm and 940 nm. The injection currents are supplied by current sources 35, 36 and to achieve amplitude modulation of the output of the semiconductor lasers the injection currents through the separate semiconductor lasers are amplitude modulated by way of a modulator 37. The fiber coupler 30 combines infrared light of different wavelengths from the semiconductor injection lasers into infrared light having two radiation components having the first and second wavelengths, respectively. The output light from the fiber coupler 30 is guided into the source fiber 5, which supplies the light having radiation components of different wavelengths into the woman's breast.

A simple amplitude modulation is achieved in that the modulator alternately switches on and off the respective injection currents through the separate lasers; in fact the output of both lasers is then amplitude modulated in antiphase with a square wave amplitude modulation. In this mode of operation, the CCD-sensor 4 consecutively receives the separate radiation components of the first and second wavelengths one after the other from the woman's breast. The read-out register 8 is coupled with the modulator 37 so that sets of the electrical charges formed by the successive radiation components are read-out one after the other. In this way the read-out register 8 is synchronized with the amplitude modulation. The amplifier 20 forms successive photodetector signals relating to the separate radiation components. The signal processing unit 9 comprises a buffer unit in which a first image signal that is derived from the first of successive photodetector signals is temporarily stored. The signal processing unit also comprises a subtracter unit which arranged to subtract a second image signal that is derived from next photodetector signals from the first image signal. The difference between the second and first image signal is an image signal corresponding the separate radiation components so as to form the image signal which contains spectroscopic inforamtion as well as information on the location of one or more objects within the breast tissue.

Figure 2:
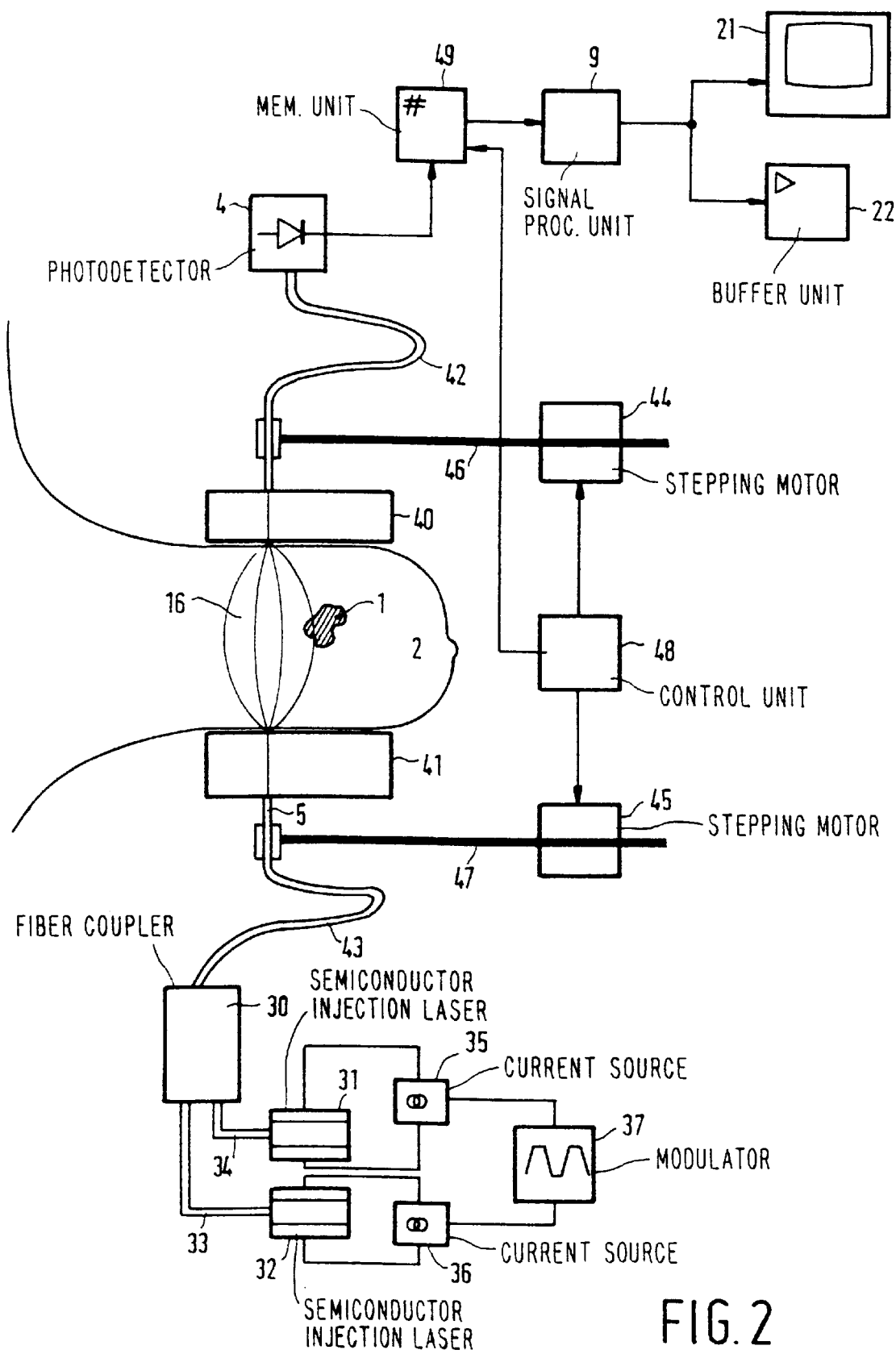
FIG. 2 shows schematically of a mammography apparatus comprising a second embodiment a system for detecting an object in a turbid medium according to the invention.

FIG. 2 shows schematically of a mammography apparatus comprising a second embodiment a system for detecting an object in a turbid medium according to the invention. The woman's breast is compressed between two perspex plates 40, 41 which form the compression apparatus. Hence, the breast tissue is forced in a slab geometry having a thickness of about 6 cm. For example, the woman's breast is compressed in a mediolateral or a craniocaudal direction. The source fiber, one end of which forms the radiation emitting face of the radiation source, emits the first and second radiation components through the perspex plates into the breast tissue. The detector fiber 7, which forms the radiation receiving portion of the photodetector, is arranged accurately, within 0.5 μm, opposite the source fiber 5. Both the detector fiber 7 and the source fiber 5 are displaceable with respect to the woman's breast, in the present embodiment by scanning the detection and source fibers together substantially parallel to the respective perspex plates 40, 41. To that end the detector fiber 7 comprises a flexible fiber portion 42 which couples the source fiber 5 to the photodetector 4 and the source fiber comprises a flexible fiber portion 43 which supplies light from the fiber coupler 30 to the source fiber 5. The source and detector fibres are mechanically coupled to respective drive means, such as stepping motors 44, 45. The mechanical coupling are e.g. rods 46, 47 to which the source and detector fibres, respectively, are mounted. The rods are moveable by means of the stepping motors. The stepping motors 44, 45 are controlled by a control unit 48 which is arranged to move the source and detector fiber together in such a way that they remain accurately positioned opposite one another.

Photodetector signals for photodetector 4 pertaining to successive positions of the source and detector fibers are stored in a memory unit 49 at respective addresses. To that end the control unit 48 supplies an addressing signal relating to the position of the source and detector fibers to the memory unit 48. The successive photodetector signals are applied to the image processing unit 9 which derives the image signal that represents the position and information on the composition of the object 1 in the turbid medium 2. The information carried by the image signal is displayed on the monitor 21 and/or the image signal is temporarily stored in the buffer unit 22 before further processing.

Although the invention is described here by way of example for a mammography system, it is evident to the skilled person will infer that the invention may also be advantageously used for examination of other parts of a human or animal body.

I claim:

1. A system for detecting an object present in a turbid medium comprising:
   a radiation source for irradiating a turbid medium with radiation comprising radiation components of a first and a second wavelength, wherein the radiation components of the first and second wavelength are modulated with amplitude modulation at substantially equal modulation frequencies, the amplitude modulation of the radiation components of the first and second wavelength having a predetermined and fixed phase difference, and
   a photodetector arranged to detect an intensity signal of radiation emerging from the turbid medium.

2. A system as claimed in claim 1, wherein the predetermined phase difference is substantially equal to 180°.

3. A system as claimed in claim 1, wherein the photodetector has a sensitivity wavelength range encompassing the first and second wavelength.

4. A system as claimed in claim 1, wherein the amplitude modulation is substantially a square wave modulation.

5. A system as claimed in claim 1, further comprising
   a compression mechanism for compressing the turbid medium, and
   a displacement device for moving a radiation emitting face with respect to the turbid medium, and wherein the photodetector has a radiation receiving portion which is arranged opposite said radiation emitting face.

6. A system as claimed in claim 1, comprising a source fiber arranged for guiding radiation from the radiation source to the turbid medium, and a plurality of detector fibers arranged for guiding radiation to the photodetector from respective positions of the turbid medium.

7. A system as claimed in claim 6, wherein the photodetector is a charge-coupled device (CCD).

8. A system as claimed in claim 1, wherein the photodetector comprises a read-out circuit that is arranged to operate synchronously with the amplitude modulation.

9. A system as claimed in claim 8, wherein the read-out circuit comprises a subtraction unit.

10. A method for detecting an object in a turbid medium comprising:
    irradiating a turbid medium with radiation components having a first and a second wavelength, respectively, wherein the radiation components of the first and second wavelength are modulated with amplitude modulation at substantially equal modulation frequencies, the amplitude modulation of the radiation components of the first and second wavelength having a predetermined and fixed phase difference, and
    detecting an intensity signal of radiation emerging from the turbid medium,
    determining the presence of an object when the detected intensity signal deviates from a predetermined intensity signal.

11. A system as claimed in claim 2, wherein the photodetector has a sensitivity wavelength range encompassing the first and second wavelength.

12. A system as claimed in claim 2, wherein the amplitude modulation is substantially a square wave modulation.

13. A system as claimed in claim 3, wherein the amplitude modulation is substantially a square wave modulation.

14. The system of claim 1 wherein the amplitude modulation and the predetermined phase difference are such that (I) in the case no object is present in the turbid medium the total of the detected intensities has practically only a DC component, and (ii) in the case an object is present in the turbid medium the total of the detected intensities comprises an AC component at the amplitude modulation frequency.

15. The system of claim 1 wherein both radiation components are incident on the turbid medium at a same position.

16. The system of claim 1 further comprising a signal processing unit for processing the detected intensity signal and its deviation from a predetermined intensity signal into an image signal.

17. The system of claim 16 wherein the amplitude modulation and the predetermined phase difference are such that the predetermined intensity signal has practically only a DC component.

18. The method of claim 10 further comprising a step of selecting the amplitude modulation and the predetermined phase difference so that the predetermined intensity signal has practically only a DC component, and wherein the step of determining determines the presence of an object in the turbid medium when the detected intensity signal comprises an AC component at the amplitude modulation frequency.

19. The method of claim 10 wherein both radiation components are incident on the turbid medium at a same position.

20. The method of claim 10 wherein the predetermined phase difference is substantially equal to 180°.

21. The method of claim 10 wherein the amplitude modulation is substantially a square wave modulation.

* * * * *